United States Patent
Perry

(10) Patent No.: US 11,786,353 B2
(45) Date of Patent: *Oct. 17, 2023

(54) CORNEAL GRAFT ASSEMBLIES FOR IMPROVED SURGICAL OPERATIONS

(71) Applicant: The North Carolina Eye Bank Inc(Miracles In Sight), Winston-Salem, NC (US)

(72) Inventor: Isaac L Perry, Winston-Salem, NC (US)

(*) Notice: Subject to any disclaimer, the term of this patent is extended or adjusted under 35 U.S.C. 154(b) by 218 days.

This patent is subject to a terminal disclaimer.

(21) Appl. No.: 16/989,057

(22) Filed: Aug. 10, 2020

(65) Prior Publication Data

US 2021/0045863 A1 Feb. 18, 2021

Related U.S. Application Data

(62) Division of application No. 16/392,259, filed on Apr. 23, 2019, now Pat. No. 10,806,558.

(51) Int. Cl.
*A61F 2/14* (2006.01)
*A61F 9/007* (2006.01)
*A61F 2/00* (2006.01)

(52) U.S. Cl.
CPC .......... *A61F 2/0095* (2013.01); *A61F 2/142* (2013.01); *A61F 2/148* (2013.01); *A61F 9/007* (2013.01)

(58) Field of Classification Search
CPC ........ A61F 2/0095; A61F 2/142; A61F 2/148; A61F 9/007; A01N 1/0273
See application file for complete search history.

(56) References Cited

U.S. PATENT DOCUMENTS

| 8,029,515 B2 | 10/2011 | Shiuey |
| 8,470,029 B2 * | 6/2013 | Walter ............... A61F 2/142 |
| | | 623/6.12 |
| 9,999,497 B2 | 6/2018 | Shiuey |
| 10,041,865 B2 | 8/2018 | Tran |
| 2010/0057093 A1 | 3/2010 | Ide et al. |
| 2013/0085567 A1 | 4/2013 | Tan et al. |
| 2013/0274875 A1 | 10/2013 | Ide et al. |

(Continued)

FOREIGN PATENT DOCUMENTS

| CH | 708083 A1 | 11/2014 |
| GB | 2521360 A | 6/2015 |

(Continued)

OTHER PUBLICATIONS

Prekh, Mohit et al. Preloaded Tissues for Descemet Membrane Endothelial Keratoplasty American Journal of Ophthalmology, 2016, vol. 166, 120-125.

(Continued)

*Primary Examiner* — William H Matthews
(74) *Attorney, Agent, or Firm* — ePatentManager.com; Guerry L. Grune

(57) ABSTRACT

Assemblies for storing, handling, transporting, viewing, evaluating, and/or shipping corneal tissue are provided. The assembly includes a corneal tissue carrier within a vial, the transport vial removably coupled to a stabilization base, wherein the ease of access to the graft carrier allows administering the corneal tissue sample to a patient in rapid succession so that more surgeries can be performed by a single surgeon in a single day.

5 Claims, 4 Drawing Sheets

(56) References Cited

U.S. PATENT DOCUMENTS

| | | | |
|---|---|---|---|
| 2013/0317605 A1 | 11/2013 | Ide et al. | |
| 2017/0095325 A1 | 4/2017 | Plambeck et al. | |
| 2017/0340428 A1 | 11/2017 | Szurmann et al. | |
| 2019/0038400 A1 | 2/2019 | Samudre | |
| 2020/0206029 A1* | 7/2020 | Abdullayev | ............ A61F 2/142 |

FOREIGN PATENT DOCUMENTS

| | | |
|---|---|---|
| WO | 2008096821 A1 | 8/2008 |
| WO | 2012065602 A2 | 5/2012 |
| WO | 2017201213 A1 | 11/2017 |
| WO | 2018208729 A1 | 11/2018 |

OTHER PUBLICATIONS

Busin, Massimo et al. Contact Lens-Assisted Pull-Through Technique for Delivery of Tri-Folded (Endothelium in) DMEK Grafts Minimizes Surgical Time and Cell Loss. Ophthalmology, 2016, vol. 123, Issue 3, 476-483.

Geuder Pre-Loaded Glass Cannula for DMEK. https://corneagen.com/Corneal-Products/Pre-loaded.aspx. (accessed Feb. 4, 2019).

Stuart, Annie, Is DMEK on the Rise? EYENET. Dec. 2013. p. 40-46.

DMEK Surgical Disposable Set. Dutch Ophthalmic. https://www.ophthalmologyweb.com/Refractive/6046-Endothelial-Keratoplasty-DSEK-DSAEK-Instruments/?vendor=9616. (accessed Feb. 4, 2019).

DMEK: Techniques & Tools. Ophthalmology Management, Nov. 2016.

Deng, et al., Clinical Outcomes of Descemet Membrane Endothelial Keratoplasty Using Eye Bank-Prepared Tissues American Journal of Ophthalmology. Mar. 2015: pp. 590-596.

Rickmann, A., Wahl, S., Katsen-Globa, A. et al. Int Ophthalmol, pp. 1-7. (Jan. 2019).

Preloaded Tissues for Descemet Membrane Endothelial Keratoplasty, https://entokey.com/preloaded-tissues-for-descemet-membrane-endothelial-keratoplasty/. (accessed Feb. 4, 2019).

Arenas, E, et al. Lamellar Corneal Transplantation. Survey of Ophthalmology. vol. 57, No. 6, Nov.-Dec. 2012. p. 510-529.

Arnalich-Montiel, F., et al. Double port injector device to reduce endothelial damage in DMEK. Eye (2014) 28, 748-751; doi:10.1038/eye.2014.67; published online Mar. 28, 2014.

Pre-Loaded DMEK Tissue/DMEK Connect. Eversight Services. Promotional Material. Revised Sep. 28, 2018.

Romano, V., Pareka, M., Ruzza, A., et al. Comparison of preservation and transportation protocols for preloaded Descemet membrane endothelial keratoplasty. Br J Ophthalmol 2018;102:549-555.

Terry, M.A., Straiko, M.D., Veldman, P.B., et al. Standardized DMEK technique: reducing complications using prestripped tissue, novel glass injector, and sulfur hexafluoride (SF6) gas. Cornea, 34 (2015), pp. 845-852.

Dapen, I., Moutsouris, K., Droutsas, K., et al. Standardized "no-touch" technique for Descemet membrane endothelial keratoplasty. Arch Ophthalmol, 129 (2011), pp. 88-94.

Melles,, et al., Transplantation of Descemet's Membrane Carrying Viable Endothelium Through a Small Sclera Incision, Cornea_ Lippincott Williams & Wilkins, Inc. vol. 21, No. 4, 2002: pp. 415-418.

Melles, et al., Descemet Membrane Endothelial Keratoplasty (DMEK)., Cornea_ Lippincott Williams & Wilkins_ vol. 25, No. 8, Sep. 2006: pp. 987-990.

Price, et al., Descemet Membrane Endothelial Keratoplasty, International Ophthalmology Clinics_ vol. 50, No. 3, 2010: pp. 137-147.

Hamzaoglu, et al., The First 100 Eyes of Standardized Descemet Stripping Automated Endothelial Keratoplasty Versus Standardized Descemet Membrane Endothelial Keratoplasty., Elsevier, Inc. American Academy of Ophthalmology. 2015: pp. 2193-2199.

\nshu, et al., Risk of Corneal Transplant Rejection Significantly Reduced with Descemet's Membrane Endothelial Keratoplsty, Elsevier, Inc. American Academy of Ophthalmology, 2012, pp. 536-540.

Guerra, et al., Descemet's Membrane Endothelial Keratoplasty: Prospective Study of 1-Year Visual Outcomes, Graft Survival, and Endothelial Cell Loss, Elsevier, Inc., American Academy of Ophthalmology. 2011: pp. 2368-2373.

Guerra, et al., Endothelial Keratoplasty: Fellow Eyes Comparison of Descemet Stripping Automated Endothelial Keratoplasty and Descemet Membrane Endothelial Keratoplasty, Cornea. Lippincott Williams & Wilkins. vol. 30, No. 12, Dec. 2011: pp. 1382-1386.

Ham, et al., Visual Rehabilitation Rate After Isolated Descemet Membrane Transplantation, American Medical \ssociation. vol. 127, No. 3, Mar. 2009: ppg. 252-255.

Eye Bank Association of America. 2018 Eye Banking of America Statistical Report. Washington D.C.: Eye Bank Association of America; 2019.

* cited by examiner

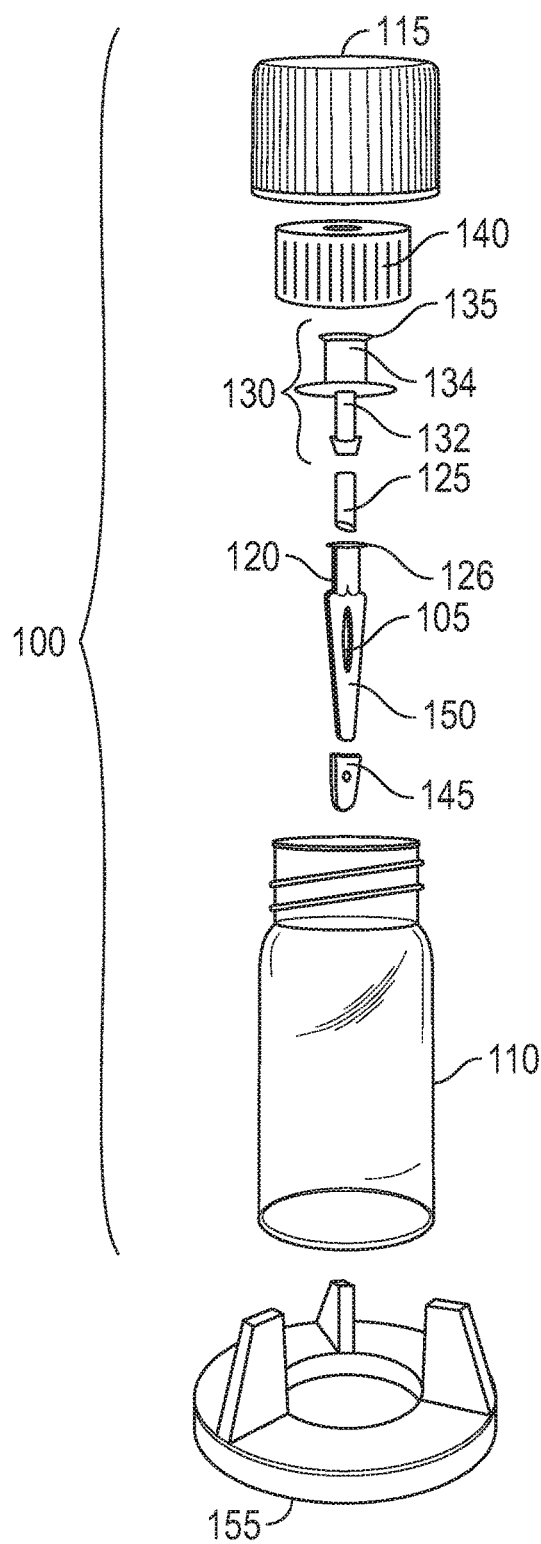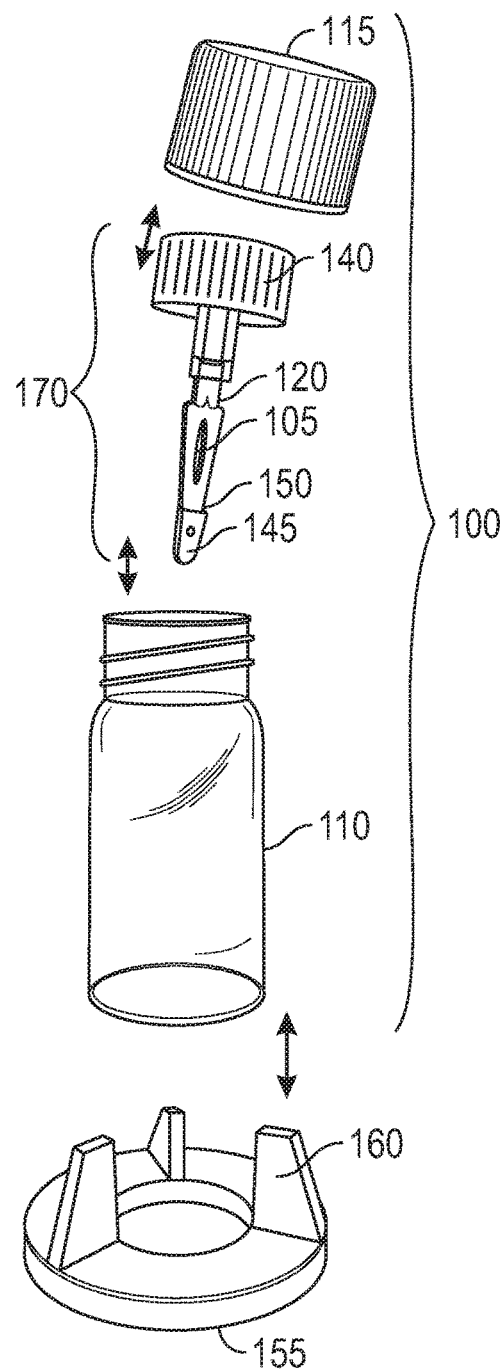
FIG. 1A
FIG. 1B

CORNEAL GRAFT ASSEMBLIES FOR IMPROVED SURGICAL OPERATIONS

PRIORITY

This application is a divisional of and claims priority under US 35 USC 120 from U.S. application Ser. No. 16/392,259, entitled "Corneal Graft Assemblies for Improved Surgical Operations", and filed Apr. 23, 2019.

The above mentioned applications are hereby incorporated by reference in their entirety.

DESCRIPTION

Technical Field

The present disclosure relates generally to corneal tissue graft assemblies. More specifically, the present disclosure relates to human or animal tissue sample devices that allow for storage, handling, transportation, visualizing and/or evaluation of the tissue prior to and during surgical operations. Even more specifically, the present disclosure provides for use of the devices with corneal tissue. The present disclosure also relates to surgical method(s) optimization using such devices for administering corneal tissue grafts to subjects in need thereof.

Background

Descemet's Membrane Endothelial Keratoplasty (DMEK) is a corneal transplantation procedure that enables a one-for-one replacement of a diseased Descemet's membrane and endothelium complex (see Melles G R, et al. Cornea. 2002; 21:415-418; Melles G R, et al. Cornea. 2006; 25:987-990; and Price M O, et al. Int Ophthalmol Clin. 2010; 50:137-147). DMEK may provide improved postoperative visual outcomes, faster recovery times, and reduced rates of rejection compared to other endothelial keratoplasty procedures such as Descemet's Stripping Automated Endothelial Keratoplasty (DSAEK) and Penetrating Keratoplasty (PKP) (see Hamzaoglu E C, et al. Ophthalmology. 2015; Anshu A, et al. Ophthalmology. 2012; 119: 536-540; Guerra F P, et al. Ophthalmology. 2011; 118:2368-2373; Tourtas T, et al. Am J Ophthalmol. 2012; 153:1082-1090 e1082; Guerra F P, et al. Cornea. 2011; 30:1382-1386; and Ham L, et al. Arch Ophthalmol. 2009; 127:252-255). While DSAEK and PK remain the most widely performed corneal transplant procedures worldwide, DMEK is steadily gaining ground on these and other surgical procedures in the United States (see Eye Bank Association of America. 2018 Eye Banking of America Statistical Report. Washington D.C.: Eye Bank Association of America; 2019).

With DMEK gaining popularity among surgeons, eye banks have developed internal processing programs to assist surgeons in preparing DMEK grafts (see Eye Bank Association of America. 2018 Eye Banking of America Statistical Report. Washington D.C.: Eye Bank Association of America; 2019; Holiman J, et al. In: Mohit Parekh.; Stefano Ferrari D P, ed. Eye Banking: Nova Biomedical; 2015:123-139; Deng S X, et al. Am J Ophthalmol. 2015; 159:590-596; and Terry M A, et al. Cornea. 2015; 34:845-852). Eye bank prepared pre-stripped, pre-peeled, and/or pre-loaded tissues can help reduce both time in the operating room (OR) and potential complications that may arise if tissue preparation fails during surgery. Pre-stripped, pre-peeled, and/or pre-loaded tissues can also provide an additional level of quality assurance as eye banks can perform post-processing evaluation of grafts using tissue evaluation instruments and methods, such as, specular microscopy, slit-lamp biomicroscopy, light microscopy, and/or optical coherence tomography, which are not typically performed in the OR.

US Patent Application No. 2017/0340428 provides a corneal tissue storage and transport kit, where a graft carrier is removably secured to a transport bracket positioned in a 50 mL flask. The glass graft carrier, capped on each end, is removed from the transport bracket using a counter-resistive prying force. The graft carrier has one end tapered for insertion into the surgical site, while the opening on the opposing end is larger and non-tapered allowing for the graft carrier to slip onto a syringe. The device comprises a container, which can be filled with a medium, preferably a nutrient medium, and a receiving device, which can be arranged in the container for the graft or implant. The graft or implant is arranged in a separate receiving device in the container. As a result, the graft or implant is securely handled by means of the receiving device and, at the same time, the graft or implant secured in the receiving device is protected in the container.

U.S. Pat. No. 10,041,865 provides an assembly for storing and evaluating corneal tissue, the assembly having a viewing chamber with a body and a lid; and a corneal tissue carrier removably coupled to an inner portion of the body of the viewing chamber. A corneal tissue sample assembly is also described as having an inner cavity with an opening on each end to which two removable plugs are provided to close or seal the corneal tissue sample within the cavity.

Therefore, the present disclosure includes the objective of providing a device and a set that is an assembly of sterile components which allow for a secure support and/or secure transport, as well as providing a secure and simple graft or implant as the graft or implant is introduced into a human or an animal body.

Benefits of the present disclosure include significant volume reduction of storage medium, locking connection(s) between the tissue transport assembly and syringe, flexibility of access to the tissue transport assembly, elongated tissue transport device, and a stabilizing device. Such benefits allow for a notable time savings, which can lead to an increase in the number of surgeries performed by a capable surgeon in a given day.

Further safety advantages are offered in the present disclosure. Breakage of glass graft carriers may occur when the graft carrier is directly engaged by forceps or hemostats and/or pried loose from prongs used to secure the carrier during transport, such as in other commercially available graft devices/kits provided and described above. Elimination of breakage is successful through forcep engagement of the graft carrier at the cap of the luer-locking device, preventing the need for a metal to glass interaction. Breakage is also eliminated as there is no coupling of the graft carrier to the vial or any form of transport bracket, thereby eliminating the counter-resistive force required to remove the graft carrier from the coupling. Minor compression forces secure the present disclosure in a safe manner such that the force is relieved upon opening the vial lid.

Financial benefits include the volume reduction of storage medium by at least one-third of the used volume for at least one earlier device, as well as a reduction in surgical time. A vial of storage medium is typically provided in 20 mL volumes at approximately $40-$50 per vial. The storage and transport kit provided herein requires no more than a single vial of storage medium where other currently available kits may use up to 3 vials of storage medium. Additionally, the reduction in surgical time translates to hospital or surgical center cost savings, while performing more reliable procedures per day. Quicker surgery often translates to greater efficiency with respect to patient anesthesia dosing. The use of the present assemblies and associated operating procedures also provide for increased revenue for the hospital and/or clinic where the procedures are performed.

Preservation of the graft near a sterile field is achieved through a stabilizing base that provides support to prevent spillage while maintaining a proper preferred position of the graft carrier. The tapering and elongation of the graft carrier assembly reduces the likelihood of aspiration of the graft into a syringe before and/or during the surgical procedure.

SUMMARY

Assemblies for storing, handling, transporting, viewing, evaluating, and/or shipping corneal tissue are provided. The assembly includes a corneal tissue carrier within a vial, the transport vial removably coupled to a stabilization base, wherein the ease of access to the graft carrier allows administering the corneal tissue sample to a patient in rapid succession so that more surgeries can be performed by a single surgeon in a single day.

More specifically, the present disclosure describes a kit comprising components that together complete a fitted assembly for supporting and transporting a graft or implant wherein the kit comprises; a vial with a lid that includes a poly-cone insert, a support base that provides support so that the vial is able to stand upright and remain motionless, a collarless luer locking cap that includes a female luer lock section and a connection portion that includes both a female luer locking end and a barbed male end, wherein the female luer locking end connects with the luer locking cap and wherein the barbed male end is slideably coupled to tubing that is further connected to a tissue carrier thereby providing a completed fitted assembly.

In another embodiment, the female luer locking end connects with a syringe after the collarless luer locking cap has been removed so that the completed fitted assembly provides an ability to directly insert tissue into a patient's eye, specifically an anterior chamber and/or cornea by a surgeon, and wherein the tissue is held within the tissue carrier with a flexible cap with orifices arranged circumferentially and perpendicular to an opening of the tissue carrier that is removably coupled with a tapered end of the tissue carrier.

In another embodiment, the tissue carrier is a corneal tissue carrier that carries corneal tissue and wherein the corneal tissue carrier is a modified ophthalmic tube that includes a Jones tube or other modified tube-shaped device.

In yet another embodiment, the collarless luer locking cap includes a small indention that accepts a tip of at least one of a group consisting of forceps, microforceps, hemostat, and suitable sterile device that allows for ease of grasp of the tissue from the completed fitted assembly and ease of retrieval of the tissue from the vial and wherein the vial has a base that is either a circular or square-shaped, or the vial is cylindrical and includes at least one flat plane portion.

In another embodiment, the tissue carrier is comprised of either transparent or translucent glass, thermoplastics, and/or silicone polymers, and is designed to hold a lamellar cornea graft, that may be a scrolled corneal tissue graft, from either a primary cell donor or obtained via ex vivo cellular expansion methods that can be seen and inspected by a surgeon prior to and during an operation that utilizes the corneal tissue.

In another embodiment, the tubing can be flexible and pliable tubing and wherein the tubing comprises materials that are flexible, pliable or rigid materials selected from one or more of a group consisting of silicone, silicone rubber, thermoplastics, thermosets, metals, and ceramics.

In another embodiment, the syringe is optionally included with the kit.

A complete fitted assembly for supporting and transporting a graft or implant wherein the assembly comprises; a vial with a lid that includes a poly-cone insert, a support base that provides support so that the vial is able to stand upright and remain motionless, a collarless luer locking cap that includes a female luer lock section and a connection portion that includes both a female luer locking end and a barbed male end, wherein the female luer locking end connects with the luer locking cap and wherein the barbed male end is slideably coupled to tubing that is further connected to a tissue carrier thereby providing a completed fitted assembly.

In another embodiment of the assembly, the female luer locking end connects with a syringe after the collarless luer locking cap has been removed so that the completed fitted assembly provides an ability to directly insert tissue by a surgeon, and wherein the tissue is held within the tissue carrier.

In another embodiment of the assembly, the tissue carrier is a corneal tissue carrier that carries corneal tissue and wherein the corneal tissue carrier may be a modified Jones tube or a modified tube-shaped device.

In another embodiment of the assembly, the collarless luer locking cap includes a small indention that accepts a tip of at least one of a group consisting of: forceps, microforceps, hemostat, and suitable sterile device that allows for ease of grasp of the tissue from the completed fitted assembly and ease of retrieval of the tissue from the vial and wherein the vial has a base that is either a circular or square-shaped, or the vial is cylindrical and includes at least one flat plane portion.

In another embodiment of the assembly, the tissue carrier is comprised of either transparent or translucent glass, thermoplastics, and/or silicone polymers, and is designed to hold a lamellar cornea graft, that includes a possibly scrolled corneal tissue graft, from either a primary cell donor or obtained via ex vivo cellular expansion that can be observed and inspected by a surgeon prior to and during an operation that utilizes the corneal tissue.

In another embodiment of the assembly, the tubing can be flexible and pliable tubing and wherein the tubing comprises materials that are flexible, pliable or rigid materials selected from one or more of a group consisting of silicone, silicone rubber, thermoplastics, thermosets, metals, and ceramics.

A method for performing tissue repair or replacement surgery that includes utilizing a fitted assembly within a vial filled with storage media fluid and a graft or implant for supporting and transporting the graft or implant such that when a graft or implant held within the assembly arrives for surgery, a surgeon inspects the graft or implant and the surgeon simply retrieves the fitted assembly that functions as a graft or implant carrier, removes a luer locking cap and attaches a syringe filled with a balanced salt solution (BSS) to a female luer locking connector wherein the fitted assembly includes flexible tubing and an inlet luer-locking mechanism allowing the surgeon quick and simple access to the graft or implant and immediate completion of surgery to replace or repair the tissue.

In another embodiment of the method, the tissue repair or replacement surgery is a lamellar keratoplasty surgery utilizing primary cells from a donor, or cells that are obtained via ex vivo methods, which in often includes endothelial keratoplasty, specifically, DMEK surgery.

A method of using a completed fitted assembly for supporting and transporting a graft or implant that is a tissue wherein the assembly comprises; a vial with a lid that includes a poly-cone insert, a support base that provides support so that the vial is able to stand upright and remain motionless, a collarless luer locking cap that includes a female luer lock section and a connection portion that includes both a female luer locking end and a barbed male end, wherein the female luer locking end mates with the luer locking cap and wherein the barbed male end is slideably coupled to tubing that is further connected to a tissue carrier thereby providing a completed fitted assembly such that when the female luer locking end connects with a syringe after the collarless luer locking cap has been removed so that the completed fitted assembly provides an ability to directly insert tissue by a surgeon, and wherein the tissue is held within the tissue carrier.

In another embodiment of the method, the tissue carrier is a corneal tissue carrier that carries corneal tissue and wherein the corneal tissue carrier is a modified Jones tube or other a modified tube-shaped device and the tissue carrier includes a flexible cap with orifices arranged circumferentially and perpendicular to an opening of the tissue carrier that is removably coupled with a tapered end of the tissue carrier.

In another embodiment of the method, the collarless luer locking cap includes a small indention that accepts a tip of at least one of a group consisting of: forceps, microforceps, hemostat, and suitable sterile device that allows for ease of grasp of the tissue from the completed fitted assembly and ease of retrieval of the tissue from the vial.

In another embodiment of the method, the tissue carrier is comprised of either transparent or translucent glass, thermoplastics, and/or silicone polymers, and is designed to hold a lamellar cornea graft, that includes possibly a scrolled corneal tissue graft, from either a primary cell donor or obtained via ex vivo cellular expansion that can be observed and inspected by a surgeon prior to and during an operation that utilizes the corneal tissue.

In another embodiment of the method, the tubing can be flexible and pliable tubing and wherein the tubing comprises materials that are flexible, pliable or rigid materials selected from one or more of a group consisting of silicone, silicone rubber, thermoplastics, thermosets, metals, and ceramics.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 1A is an exploded view of a corneal tissue sample assembly with corneal tissue carrier and stabilization attachment.

FIG. 1B is an exploded view of a corneal tissue sample assembly with assembled corneal tissue carrier and stabilization attachment.

DETAILED DESCRIPTION

Figure 2:
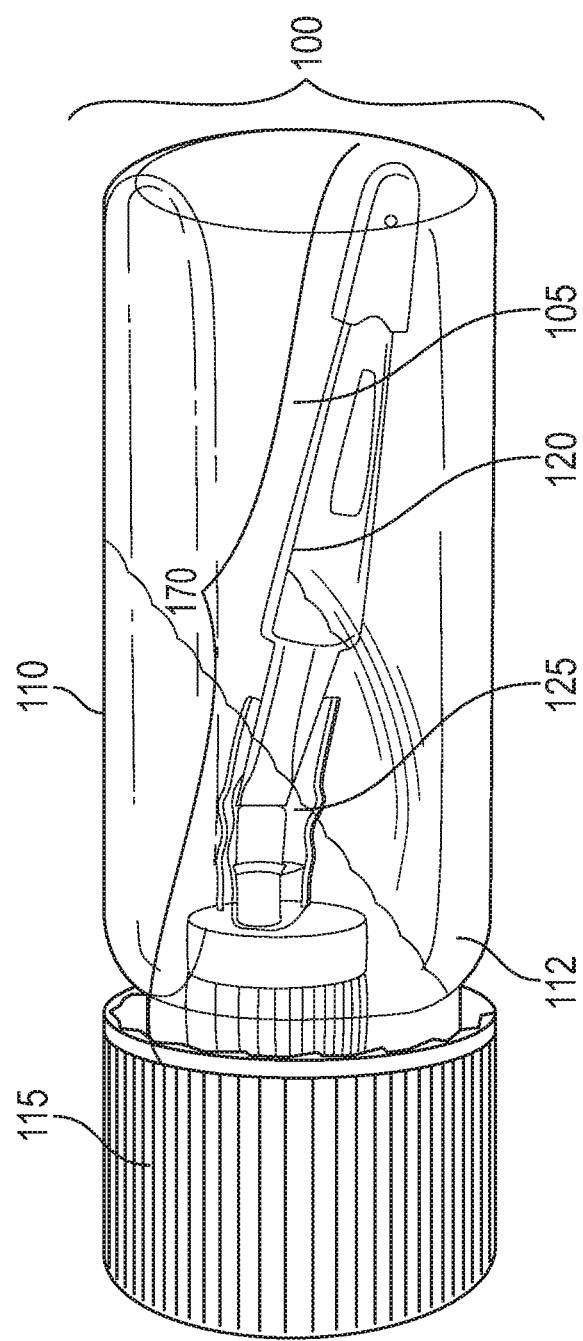
FIG. 2 is a perspective view of the corneal tissue sample assembly with corneal tissue carrier for supporting and transporting a graft.

The various embodiments disclosed herein generally relate to assemblies for storing, handling, transporting, viewing, evaluating, and/or shipping corneal tissue. The assemblies include a vial, and a corneal tissue (graft) carrier. The assemblies may also include a corneal tissue (graft) sample, wherein the corneal tissue sample is disposed within the corneal tissue carrier.

Various features of the corneal tissue sample assemblies disclosed herein may be grouped together in a single embodiment, figure, or description thereof for the purpose of streamlining the disclosure. Many of these features may be used alone and/or in combination with one another in the various embodiments.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the assembly is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component. The phrase "fluid communication" is used in its ordinary sense, and is broad enough to refer to arrangements in which a fluid (e.g., a gas or a liquid) can flow from one element to another element when the elements are in fluid communication with each other.

FIG. 1A is an exploded view of the assembly [100] for storing, handling, transporting, viewing, evaluating, and/or shipping corneal tissue [105] (also referred to herein as a graft).

Figure 4:
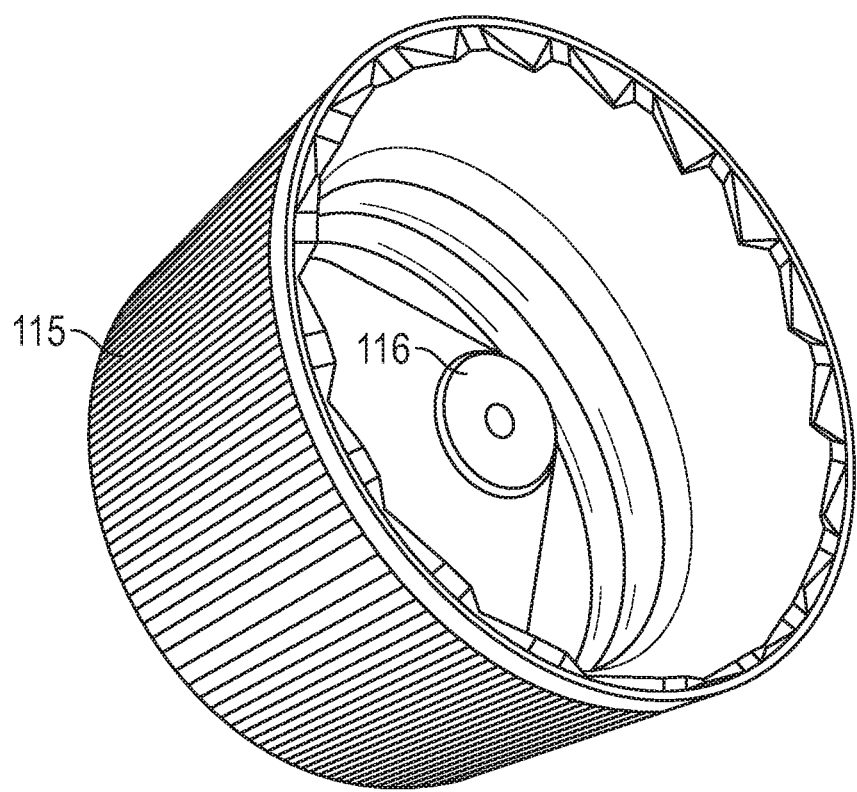
FIG. 4 is a view of a poly-cone insert inside the lid intended for the vial seen in FIGS. 1A-3.

The assembly [100] for transporting a corneal graft [105] is prepared for endothelial keratoplasty. There exists a clear vial [110], also referred to as "the vial", which when assembled will contain 18-22 mL of cornea storage media [112], and a vial lid [115], preferably with a poly-seal cone insert (FIG. 4) on the interior side of the lid. The vial may have a base that is a rounded shape, a square shape, or the vial may be cylindrical with at least one flat plane positioned as a chord along the circumference of its surface.

The assembly [100] further includes a corneal tissue carrier, or graft carrier [120]. In certain embodiments, the corneal tissue carrier [120] may be a Straiko modified Jones tube, a Jones tube, derivatives thereof, or another suitable tissue carrier. In one embodiment, the corneal tissue carrier [120] may be a modified Jones tube for DMEK, and will have rounded or oval openings measuring 2-5 mm in diameter, one of which is beveled and measures 1-3.5 mm in diameter, and 36-40 mm in length. In some embodiments, the corneal tissue carrier [120] may be formed from a polymer, a glass, or another suitable material. In specific embodiments, the corneal tissue carrier [120] may be formed from a biocompatible material (e.g., a biocompatible polymer, a biocompatible glass, etc.).

The corneal tissue [105] is housed inside of an assembly [100] consisting of a transport assembly provided as a corneal tissue carrier [120], with flexible tubing [125] attached to a larger, ringed end [126] of the corneal tissue carrier [120]. A connecting device [130] consisting of both a barbed male end [132], and a female end luer locking connector [134] with an inlet luer locking mechanism [135], is removably coupled to the ringed end [126] of the graft carrier [120] via the flexible tubing [125]. A luer locking cap [140] is designed to screw onto the female luer locking connector [134] of the inlet luer locking mechanism [135]. A flexible cap [145], with holes arranged circumferentially (that may or may not be opposite each other) and perpendicular to the opening of the graft carrier [120], is removably coupled to the tapered end [150] of the graft carrier [120].

The caps [140, 145] may inhibit or restrict passage of a corneal tissue [105] out of the corneal tissue carrier [120]. In some embodiments, the caps [140,145] may allow or permit passage of fluid (e.g., a preservation fluid) into and/or out of the corneal tissue carrier [120]. In various embodiments, the caps [140, 145] may include one or more apertures (e.g., openings).

Any combination of caps or plugs (e.g., caps or plugs that allow passage of fluid and/or caps or plugs that inhibit passage of fluid) may be used with the corneal tissue carrier [120] disclosed herein.

The graft carrier [120] must be retrieved from the vial [110] in an upright position, making the vial [110] subject to tipping, spillage, and often susceptible to contamination of an otherwise sterile field. In order to provide needed additional external stability to prevent requiring assistance from an additional member of the surgical team to stabilize the vial, the vial [110] is supported with a removable non-sterile base [155]. The base [155] slides onto the vial [110] alleviating the need for additional assistance in removing the graft carrier [120] from the vial [110], and preventing the surgeon from having to touch the non-sterile external surface of the vial [110], or having a circulator hold the vial [110] to prevent tipping over at the time of retrieval. The base [155] can be injection molded, 3-D printed, or manufactured by any other such means that will produce the base as a single piece.

FIG. 1B provides an exploded view of the assembly [100] with the corneal tissue carrier [120] in an assembled configuration (which is listed [170] and includes connected components of 140, 130, 125, 120, 105, and 145) for insertion into the vial [110]. The vial lid [115] secures the corneal tissue carrier [120] housing a corneal graft [105], complete with a luer locking cap [140] on one end and a flexible cap [145] on the opposite tapered end [150], within the vial [110]. The tapered end [150] of the corneal tissue carrier [120] is inserted into the vial [110], positioning the luer locking cap [140] at the opening of the vial [110].

The corneal tissue carrier [120] is not coupled to any portion of the vial [110] or vial lid [115], and is free within the vial [110], preferably maintained in place via light compression from the poly-seal cone insert (not shown) on the interior side of the vial lid [115].

The vial [110] is placed within the prongs [160] of the base [155] in order to maintain an upright position and provide stability.

FIG. 2 is a perspective view of an assembly, kit, or corneal tissue sample assembly [100] for storing, handling, transporting, viewing, evaluating, and/or shipping corneal tissue [105] in a closed, or assembled, configuration.

Transporting the corneal tissue carrier [120] with flexible tubing [125] attached to the non-capped, ringed end [126] is shown in FIG. 2. The flexible tubing [125] is 0.5-2.5 cm in length. A barbed male luer lock end having a diameter of 1/16-5/32 inches is inserted into the flexible tubing [125]. The opposite side of the barbed male connector is a female screw-on luer locking mechanism.

The graft carrier [120] is not designed to be connected directly to a syringe, and the outer edge of the graft carrier [120] cannot be inserted into the nozzle of a syringe, as the connection is secured through the use of an inlet luer-locking mechanism [135] which prevents slippage of the graft carrier [120] from the syringe (not shown) and provides fluid communication with the graft carrier [120] and fluid control. The connection of the syringe to the graft carrier [120] creates a pre-loaded syringe relieving the surgeon from having to load the graft [105] during the surgical procedure.

The syringe does not accompany the assembly [100] as a standard. Neither of the closure devices are designed for connecting a collar or an adapter.

A collarless luer locking cap [140] is placed on the female luer locking connector [134], the luer locking cap [140] possessing a small indention that will accept the tip of forceps, microforceps, hemostat, or other suitable sterile device, and allow for easy grasping of the assembly and retrieval from the vial [110]. When the graft [105] arrives to the surgeon, the surgeon must simply retrieve the graft carrier [120], remove the luer locking cap [140], and attach their own 3 or 5 mL syringe filled with balanced salt solution (BSS) to the female luer locking connector [134]. The step of including the flexible tubing [125] and the inlet luer-locking mechanism [135] saves up to 2 minutes of valuable surgeon operating room (OR) time.

FIG. 2 provides the assembly [100], complete with a corneal graft [105] within a corneal tissue carrier [120], in a closed configuration, where the corneal tissue carrier [120] and the vial [110] both contain sufficient cornea storage medium [112] to substantially immerse the graft [105] and the graft carrier [120], respectively. The cornea storage medium [112] can be disposed within at least a portion of the corneal tissue carrier [120] (e.g., when the corneal tissue carrier [120] is disposed within the vial [110]). In certain embodiments, the cornea storage medium [112] may be disposed only within at least a portion of the corneal tissue carrier [120]. In various embodiments, the cornea storage medium [112] may be disposed within the graft carrier [120] such that the corneal tissue [105] is substantially immersed in the cornea storage medium [112]. The closure is completed with the vial lid [115] compressively securing the graft carrier [120] within the vial [110], the flexible tubing [125] providing the corneal tissue carrier [120] acceptability to any angle of retrieval from the vial [110], easing the extraction for the surgeon, thus reducing retrieval time, potential for breakage of the corneal tissue carrier, and tipping of the assembly.

In certain embodiments, the cornea storage medium [112] may be OPTISOL™-GS, OPTISOL™, LIFE4° C.™ (NU-MEDIS™, Inc.), EUSOL-C™ (CORNEAL CHAMBER™, ALCHIMIA™, Sri), CORNEA COLD® (EUROBIO™), CORNISOL™ (AUROLAB™), a derivative thereof, or other suitable preservation fluid.

Figure 3:
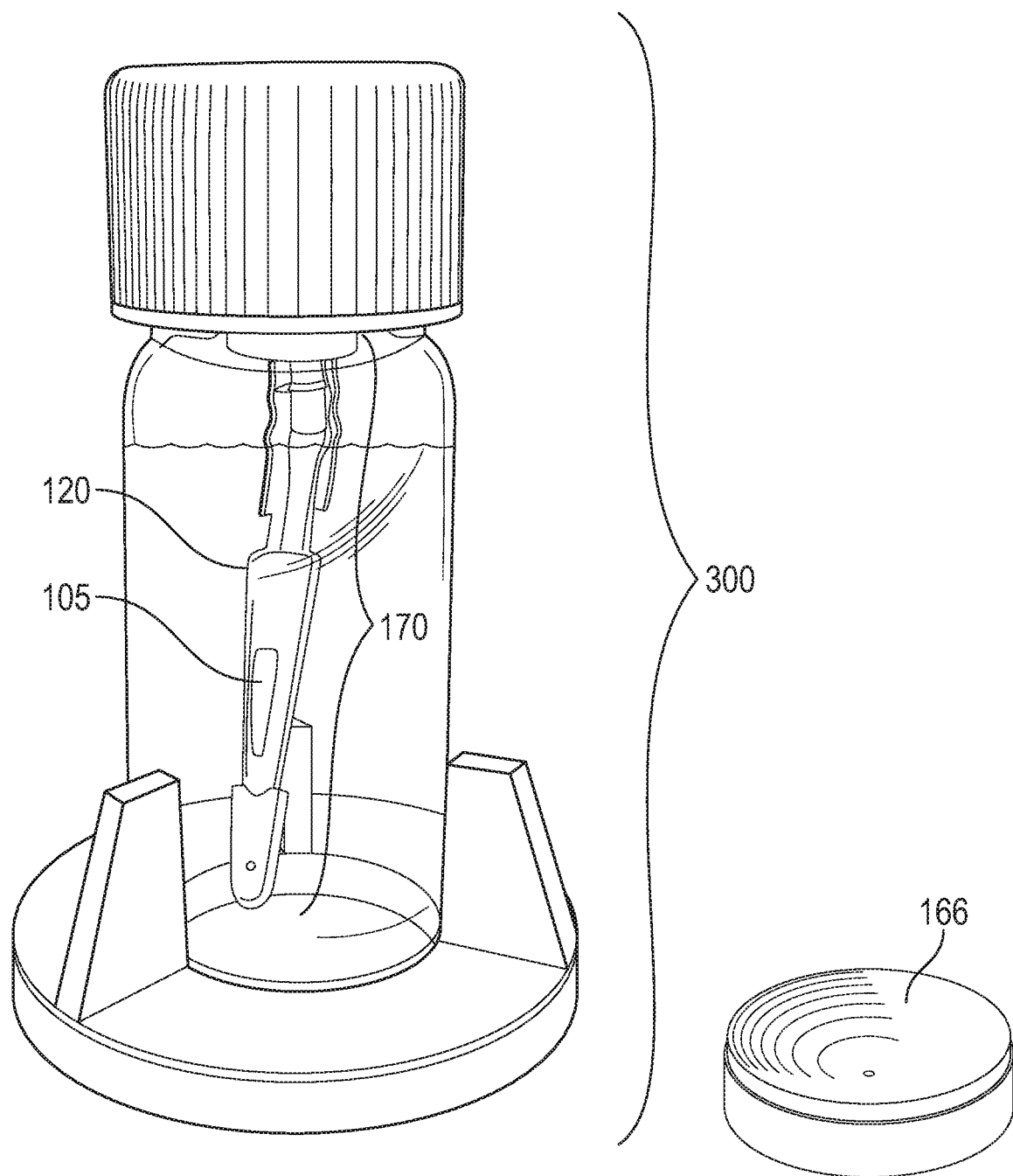
FIG. 3 is a side view of the corneal tissue sample assembly kit of FIGS. 1A-2.

FIG. 3 illustrates the assembly [110], in a closed configuration, removably coupled to the base providing a kit [300] for storing, handling, transporting, viewing, evaluating, and/or shipping corneal tissue [105]. There are non-sterile components to the kit [300], including the base [155] that provides stability for the vial during the graft carrier's [120] retrieval from the vial [100]. The loading well [166] (also referred to as a repository or disc), can be included with the kit as, for example, the corneal tissue [105] may be rinsed, examined, or aspirated into the tissue carrier [120] from this disc [166]. The loading well can be provided as a sterile addition to the kit [100]. The loading well [166] can be injection molded, 3-D printed, or manufactured by any other such means that will produce the loading well as a single piece.

It is important to understand and re-emphasize that items [145], [120], [125], [130], [140], [155] and [166] can be/may be put together as a "sterile" kit that other eye banks can use to prepare the assembly/devices described in conjunction with items [110] and [115]. The depth and shape of the loading well [166] allows for simple aspiration of the graft [105] along with an appropriate volume of storage media performed by an eye bank technician. The loading well [166] accommodates an ideal volume of storage media as it does not require opening an additional vial while ensuring the graft [105] is substantially submerged in storage media during the loading process. This loading well [166] also facilitates near-horizontal positioning of the graft carrier [120] during aspiration to minimize contact between endothelial cells and the graft carrier as the graft [105] is aspirated into the graft carrier [120] by minimizing any graft contortion as it passes through the tapered end [150] of the graft carrier [120]. This kit allows for a graft to be securely loaded, supported, and/or securely transported as well as provide a secure and simple graft or implant as the graft or implant is introduced into a human or an animal body.

The corneal tissue sample could be a pre-stained corneal tissue graft, as no further removal from the corneal tissue carrier for staining should be required prior to the attachment of the luer-locking syringe, until administration of the graft to the patient, based on surgeon preference.

The assembly [100] can further include corneal tissue [105]. The corneal tissue [105] may be suitable for various forms of keratoplasty, lamellar keratoplasty, and/or endothelial keratoplasty (e.g., DMEK, PDEK, DSAEK, Ultra-thin DSAEK, Bowman's Membrane Transplantation, etc.). In some embodiments, the corneal tissue [105] may be a graft comprising corneal endothelium and Descemet's membrane. In some other embodiments, the corneal tissue [105] may include corneal endothelium, Descemet's membrane, and/or pre-Descemet's membrane. In particular embodiments, the corneal tissue [105] may be a DMEK graft or a graft suitable for a DMEK procedure. In alternative embodiments, the corneal tissue [105] may also include stroma. The cellular structures comprising the corneal tissue [105] may be primary cells from a single donor, or cultured via ex vivo cellular expansion methodology. As shown, the corneal tissue [105] may be disposed within the corneal tissue carrier [120].

In some embodiments, at least a portion of each of the vial [110] and the corneal tissue carrier [120] may be substantially transparent, with the preferred transparency being clear, such that the corneal tissue [105] can be visible to a user. For example, the corneal tissue [105] may be disposed within the corneal tissue carrier [120], and the corneal tissue carrier [120] including the corneal tissue [105] may be further disposed within the vial [110]. In such configurations, the substantial transparency of the vial [110] and the corneal tissue carrier [120] may allow or permit the user to visualize the corneal tissue [105]. In certain embodiments, the corneal tissue carrier [120] and the vial [110] are substantially transparent and/or substantially clear such that a user may visualize and/or evaluate the corneal tissue [105] disposed within the corneal tissue carrier [120] and the vial [110] using corneal tissue evaluation instruments and/or methods such as specular microscopy, slit-lamp biomicroscopy, light microscopy, and/or optical coherence tomography.

In some embodiments, the corneal tissue carrier [120] is configured to be coupled to a syringe via a luer-locking mechanism, for example, the ringed end [126] of the corneal tissue carrier [120] is coupleable to a luer locking connector designed to accept the tip of a syringe (not shown). In certain embodiments, a portion of medical tubing may be coupled to the corneal tissue carrier [120]. In certain embodiments, the medical tubing may be integral with the corneal tissue carrier [120]. In certain other embodiments, each of the medical tubing and the corneal tissue carrier [120] may be discrete components.

A cornea storage fluid [112], or preservation fluid, can be disposed within at least a portion of the inner portion of the vial [110]. Additionally, the preservation fluid [112] can be disposed within at least a portion of the inner cavity of the corneal tissue carrier [120] such that the corneal tissue [105] is substantially immersed in the cornea storage fluid [112]

As described above, the corneal tissue sample may be a graft comprising corneal endothelium and Descemet's membrane. The corneal tissue sample may be suitable for various forms of lamellar keratoplasty (e.g., DMEK, PDEK, DSAEK, Ultra-thin DSAEK, etc.). In some embodiments, the corneal tissue sample may be a graft comprising corneal endothelium and Descemet's membrane. In some other embodiments, the corneal tissue [105] may include corneal endothelium, Descemet's membrane, and/or pre-Descemet's membrane. In particular embodiments, the corneal tissue sample is a DMEK graft or a graft suitable for a DMEK procedure. In specific embodiments, the corneal tissue sample may also include stroma. The cellular structures comprising the corneal tissue [105] may be primary cells from a single donor, or cultured via ex vivo cellular expansion methodology.

The method of processing the corneal tissue sample may also include coupling a cap to an opening of the corneal tissue carrier. As discussed above, the cap may limit or inhibit passage of the corneal tissue sample out of the corneal tissue carrier. Furthermore, the cap may allow or permit passage of the preservation fluid into and out of the corneal tissue carrier.

In some embodiments, a method of administering a corneal tissue sample may include obtaining a corneal tissue sample assembly. The assembly, as described above, may include a corneal tissue carrier and a corneal tissue sample disposed within the corneal tissue carrier. A method of administering a corneal tissue sample may further include administering or transplanting the corneal tissue sample to a subject. In some embodiments, the subject may be a patient in need of a corneal tissue transplant.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially transparent" is recited with respect to a feature, it is understood that in further embodiments, the feature can have a precisely transparent configuration.

Numerous references have been made to printed publications throughout this specification. Each of the above-cited references and printed publications is individually incorporated herein by reference in its entirety.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

I claim:

1. A method of using a completed fitted assembly for supporting and transporting a graft that is a tissue or implant that is a tissue wherein said assembly comprises; a vial with a lid that includes a poly-cone insert, a support base that provides support so that said vial is able to stand upright and remain motionless, a collarless luer locking cap that includes a female luer lock section and a connection portion that includes both a female luer locking end and a barbed male end, wherein said female luer locking end mates with said luer locking cap and wherein said barbed male end is slideably coupled to tubing that is further connected to a tissue carrier thereby providing a completed fitted assembly such that when said female luer locking end is connected to a syringe after said collarless luer locking cap has been removed, said completed fitted assembly provides an ability by a surgeon to directly insert tissue, and wherein said tissue is held within said tissue carrier.

2. The method of claim 1, wherein said tissue carrier is a corneal tissue carrier that carries corneal tissue and wherein said corneal tissue carrier is a modified Jones tube or other modified tube-shaped device and said corneal tissue carrier includes a flexible cap with orifices arranged circumferentially and perpendicular to an opening of said corneal tissue carrier that is removably coupled with a tapered end of said corneal tissue carrier.

3. The method of claim 1, wherein said collarless luer locking cap includes a small indention that accepts a tip of at least one of a group consisting of: forceps, microforceps, hemostat, and sterile device that allows for ease of grasp of said corneal tissue from said completed fitted assembly and ease of retrieval of said corneal tissue from said vial.

4. The method of claim 1, wherein said corneal tissue carrier is comprised of either transparent or translucent glass, thermoplastics, and/or silicone polymers, and is designed to hold a lamellar cornea graft, that includes a scrolled corneal tissue graft, from either a primary cell donor or obtained via ex vivo cellular expansion that is observed and inspected by a surgeon prior to and during an operation that utilizes said corneal tissue.

5. The method of claim 1, wherein said tubing is flexible and pliable tubing and wherein said tubing comprises materials selected from one or more of a group consisting of silicone, silicone rubber, thermoplastics, thermosets, metals, and ceramics.

* * * * *